United States Patent
Piasio et al.

(10) Patent No.: US 7,018,849 B2
(45) Date of Patent: Mar. 28, 2006

(54) PROCESS FOR (A) SEPARATING BIOLOGICAL/LIGANDS FROM DILUTE SOLUTIONS AND (B) CONDUCTING AN IMMUNOCHROMATOGRAPHIC ASSAY THEREOF EMPLOYING SUPERPARAMAGNETIC PARTICLES THROUGHTOUT

(76) Inventors: Roger N. Piasio, 233 Foreside Rd., Cumberland Foreside, ME (US) 04110; Nathan Turner, 197 Pleasant Ave., Apartment 5, Portland, ME (US) 04103

( * ) Notice: Subject to any disclaimer, the term of this patent is extended or adjusted under 35 U.S.C. 154(b) by 568 days.

(21) Appl. No.: 10/044,920

(22) Filed: Jan. 15, 2002

(65) Prior Publication Data

US 2003/0134434 A1    Jul. 17, 2003

(51) Int. Cl.
*G01N 33/553*    (2006.01)

(52) U.S. Cl. .......................... 436/526; 422/56; 422/57; 422/58; 435/287.2; 435/287.7; 435/287.8; 435/805; 435/810; 435/970; 436/149; 436/177; 436/514; 436/806

(58) Field of Classification Search ................ 422/56, 422/57, 58; 435/7.1, 287.2, 287.7, 287.8, 435/805, 810, 970; 436/149, 514, 526, 806, 436/177

See application file for complete search history.

(56) References Cited

U.S. PATENT DOCUMENTS

| | | | | |
|---|---|---|---|---|
| 4,230,685 A | * | 10/1980 | Senyei et al. | 436/526 |
| 4,267,234 A | * | 5/1981 | Rembaum | 428/403 |
| 4,297,337 A | * | 10/1981 | Mansfield et al. | 436/527 |
| 4,452,773 A | * | 6/1984 | Molday | 424/1.37 |
| 4,554,088 A | * | 11/1985 | Whitehead et al. | 252/62.54 |
| 4,628,037 A | * | 12/1986 | Chagnon et al. | 436/526 |
| 4,672,040 A | * | 6/1987 | Josephson | 436/526 |
| 4,795,698 A | * | 1/1989 | Owen et al. | 435/4 |
| 4,965,007 A | * | 10/1990 | Yudelson | 252/62.53 |
| 5,385,707 A | * | 1/1995 | Miltenyi et al. | 422/69 |
| 5,492,814 A | * | 2/1996 | Weissleder | 435/7.25 |
| 5,512,332 A | * | 4/1996 | Liberti et al. | 427/550 |
| 5,597,531 A | * | 1/1997 | Liberti et al. | 422/57 |
| 5,916,539 A | * | 6/1999 | Pilgrimm | 424/9.322 |
| 6,120,856 A | * | 9/2000 | Liberti et al. | 427/550 |
| 6,607,922 B1 | * | 8/2003 | LaBorde | 436/514 |
| 2003/0040124 A1 | * | 2/2003 | LaBorde | 436/514 |

* cited by examiner

Primary Examiner—Christopher L. Chin

(57) ABSTRACT

Superparamagnetic ("SPM") subunits of 1–30 nm average mean diameter (e.g. ferro fluid) subparticles are treated with a magnetically noninterfering substance capable of coating and covering them (e.g, BSA) and they spontaneously form agglomerates of about 100 nm to about 450 nm or higher average mean diameter and are then used to form complexes with target biological ligands such as viruses, contained in large volumes of liquid. The complexes are subjected to the gradient intensity of a strong magnetic field, and excess liquid is removed, where upon an immunochromatographic assay is conducted to determine the identity and/or amount of target ligand present, in which operation SPM particles that bonded to the ligand function as tags for ligand detection.

14 Claims, 1 Drawing Sheet

PROCESS FOR (A) SEPARATING BIOLOGICAL/LIGANDS FROM DILUTE SOLUTIONS AND (B) CONDUCTING AN IMMUNOCHROMATOGRAPHIC ASSAY THEREOF EMPLOYING SUPERPARAMAGNETIC PARTICLES THROUGHTOUT

This invention relates to using the same superparamagnetic particles, as more particularly described hereinafter, to concentrate biological substances believed to be sparsely present in large volumes of fluids and as labelling agents for detecting the quantity of the same biological molecules present in a fluid sample.

BACKGROUND OR THE INVENTION

Heretofore it has become common to use metallic particles having superparamagnetic properties to concentrate biological ligands resent in small amounts in large volumes of aqueous fluids, including fluids of mammalian origin such as urine. These metallic particles are often of large size (typically in the order of 1–5 μm or larger in average mean diameter) such that they cannot move, or do not move sufficiently readily, through the matrices used for either flow-through tests or lateral flow immunochromatographic ("ICT") tests such as those commonly used currently in many commercially available diagnostic tests for identifying disease causative pathogens. In instance, where such tests are to follow the initial concentration step, removal of the superparamagnetic particles used for concentration is necessary, followed by adding a target specific conjugate labelled with a chemiluminescent, fluorescent or radioactive or tag or a tag such as colloidal latex particles, colloidal gold, or another colloidal metal which couples to the biological ligand and aids in the detection thereof. The need to remove superparamagnetic particles used in ligand concentration and then subject the concentrated ligand to an identification or quantification assay often poses problems. For example, quantification of the small amount of biological ligand obtained by concentration is rendered inaccurate if even a tiny fragment of concentrated ligand clings to the particles used for concentration; by the same token, incomplete removal of a small fragment of a magnetic particle may disrupt a qualitative identification of the concentrated sample by setting up an interaction with the labelling agent chosen for use in the subsequent identification test. Even in cases where superparamagnetic particles are employed to concentrate biological ligands present in a large volumes of fluid and the nature of the subsequent identification procedure renders separation of the superparamagnetic particles unnecessary, these particles have heretofore been viewed in the art as irrelevant to the subsequent identification step.

Large sized superparamagnetic particles have been preferred for ligand concentration work, because their large size (in the order of 1 to 5 μm or more) increases the mass of material bound to the target ligand and allows the gradient field of a fixed magnet to effect separation with ease. Much smaller particles have been used in some instances but often the low mass of magnetic material that they impart to their target, requires the introduction of magnetizable columns, filters or screens as an aid to separating the target molecules from the sample.

Particles heretofore used as tags for detecting a biological ligand (regardless of whether it has been subjected to a first concentration step) are usually quite small. As already noted, this is especially true where rapid "flow-through" or lateral flow matrices having narrow pores are employed as solid phase substrates. Particularly in the lateral flow ICT format, particles used as detection markers must be small enough to migrate through the pores of the matrices and reach the immobilized binding partner of the biological ligand being detected.

The present invention is based on the discovery that there is a class of superparamagnetic particles which are small enough to function as tags for detection of biological ligands in ICT test formats where solid porous matrices are employed and also have a sufficiently large magnetic moment to function effectively as ligand concentration adjuvants. The capability of using the same particles for concentration and separation of a target ligand from a large volume of liquid and as tags for a qualitative ligand identification test or a similar test that not only identifies but quantifies the amount of ligand enables a significant increase in the sensitivity of the pre-assay concentration step. At the same time, the separation of the target ligand from interfering or inhibitory substances that may be present in the original sample is enhanced, the awkward need for removing a magnetic label is avoided and so is the equally awkward need for introducing a second label.

BRIEF DESCRIPTION OF THE INVENTION

The present invention utilizes superparamagnetic subunits of 1–30 nm in average mean diameter, such as ferrofluid subparticles, which are mixed with bovine serum albumin ("BSA") or a similar biologically and magnetically non-interfering substance capable of coating and covering such particles, whereby they form BSA-coated ferrofluid particles which spontaneously agglomerate to masses each containing a number of ferrofluid subunit "cores" or nuggets, each completely surrounded by BSA. These BSA-ferrofluid agglomerates have been found to be highly effective, at overall particle average mean diameters of at least about 100 nm ranging up to about 450 nm, and at times even higher, (1) as agents from concentrating and separating out target biological ligands from large liquid volumes in which they are initially present in trace amounts and (2) as tags for enabling detection of these target ligands, for identity confirmation purposes and/or for quantification in ICT-format assays.

DETAILED DESCRIPTION OF THE INVENTION

Figure 1:
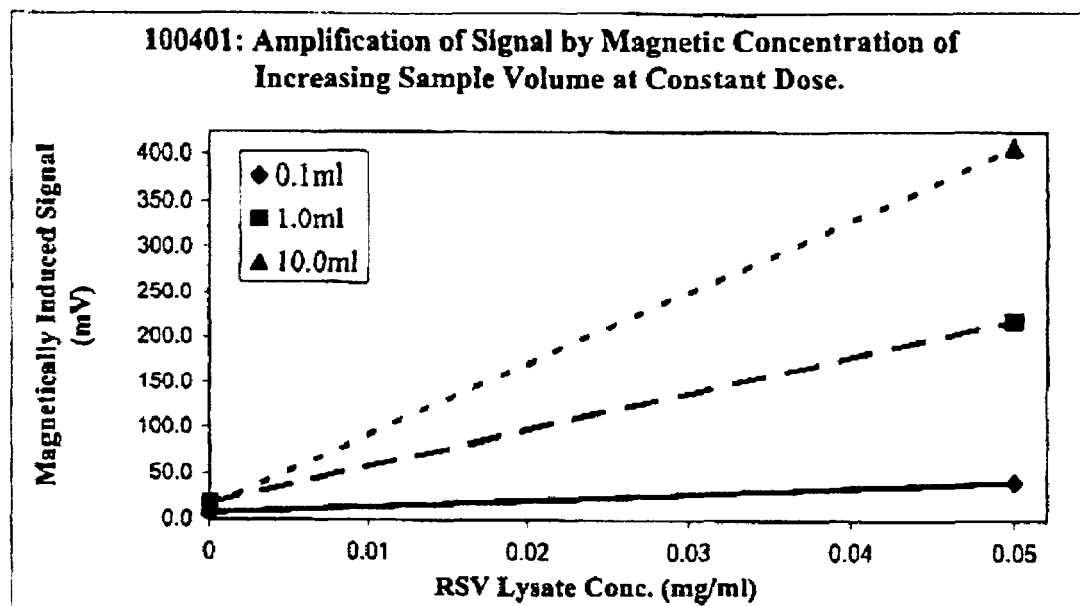
FIG. 1 hereof is a plot of magnetic signal measured in millivolts (mV) against Respiratory Syncytial Virus ("RSV") lysate in milligrams per milliliter at sample volumes of 0.1 ml., 1.0 ml. and 10.0 ml., respectively.

The vistas opened by the use of this invention are best appreciated from a consideration of the fact that the commercially available ICT assays described in the copending, commonly assigned U.S. patent application Ser. Nos. 09/139,720 and 09/397,110, which are both highly sensitive and specific for the identifying presence of particular disease-causing bacteria are successfully run with a few drops of test fluid—in the order of 100 microliters of urine, for example. Bacteria molecules, however, are large in comparison to the molecules of, e.g., viruses and various biochemical substances, the presence or concentration of which my be indicative of a disease state or another abnormal condition in a human patient.

These smaller molecules often are widely dispersed in samples of mammalian fluid, such as urine, with the result that the sample size adequate to enable detection of particular bacteria in the urine of a person suffering from a disease of which those bacteria are causative, is too dilute to insure that smaller disease-causing molecules will be equally readily detectable.

By affording a means of concentrating the smaller molecules in a liquid sample prior to assaying for them, one is enabled to detect and, if desired, quantify, the presence in, e.g., human urine, of molecules that—if run in the assay format described in the aforementioned copending applications, without preconcentration, could not be detected with high sensitivity and specificity and might not be detectable at all. Experience to date with pre-assay concentration using superparamagnetic particles composed of ferrofluid 1–30 nm diameter subunits distributed in a BSA matrix, said composite particles having average mean diameters of between at least about 100 nm and about 450 nm and coated with an antibody to the target molecule which attracts the target molecule and couples thereto, thereby effecting the desired concentration upon exposure to the gradient of a magnetic field, when followed by an ICT assay for the target molecule which assay employs the aforesaid superparamagnetic particles as tags in the assay, has demonstrated a gain of approximately 2 logarithms of sensitivity to the target molecule over results heretofore attainable with methods wherein it was attempted to perform a conventional ICT assay for the target molecule on the original sample without concentration.

The superparamagnetic material used in the investigative work described herein—i.e. ferrofluid core subunits of 1–30 nm diameter dispersed in a magnetically and biochemically inactive matrix of BSA—can be substituted as to ferrofluid by any other metallic subunits of this size range that exhibit superparamagnetic properties, including metals and metallic oxides which exhibit spinel structure alone or in combinations with one another. As already noted other materials that are magnetically inactive and in themselves biochemically unreactive with the target ligand may readily be substituted for BSA.

The procedure for concentration of a target molecule in an aqueous medium (including a mammalian bodily fluid such as urine, blood, saliva, sputum, etc.,) renders it necessary that the BSA-superparamagnetic core agglomerates having a composite particle diameter of at least about 100 nm be first coated with a material which is a binding partner for the target molecule. The coated superparamagnetic particles are then immersed in the fluid and incubated for a period of at least 15 and often 30–40 or more, minutes. Complexes of superparamagnetic particles and target ligand are thereby formed. These complexes are sequestered from the bulk of liquid sample by exposure to the gradient of a magnetic field. The liquid is then removed by aspiration, decanting or any other convenient method the particles are washed and dispersed in a volume of a suitable buffer that is smaller than the volume of the original sample. An ICT strip of nitrocellulose or other bibulous material upon which a stripe of binding partner for the target molecule—which may be the same one used in the concentration step or a different one, depending upon the functionality of the target molecule—has been immovably bound to the capture zone area, contained in a "dipstick" ICT device format, is immersed in the buffered dispersion of superparamagnetic particles complexes. Upon migration of these particles complexes along the strip, the target molecule on their outer surface binds to its binding partner in the immovable stripe, causing superparamagnetic particles to accumulate along the stripe. Experience has shown that immovable striping of binding partner for the target molecule multiple lines, spaced apart from one another along the end of the strip remote from the sample receiving end, may be appropriate to ensure efficient capture of the target ligand in this assay. The magnetic signal of the superparamagnetic tag on the capture line or lines in millivolts, is read in a suitable instrument. The instrument used for the work shown in the ensuing specific examples was a Magnetic Assay Reader IV unit obtained from Quantum Design, Inc., San Diego, Calif.

This unit is especially designed to be compatible with small volume assay formats, such as those which exhibit the end result as a line or lines of accumulated magnetic tag material. Because of the permeability of the magnetic field of the superparamagnetic tag, signal due to any analyte immobilized to the capture line is read as a single magnetic mass. This is in contrast to readings obtained from optical inspection which detect only the surface appearance of the capture line. According to the manufacturer, the magnetic reading is linear with respect to the mass of magnetic material on the capture line through at least four orders of magnitude. The construction of standard curves correlating measured magnetic signal to target ligand amount is readily achievable by methodology that is well known in the art.

It is anticipated that, for concentrating target molecules present in mammalian bodily fluids, such as, e.g. urine, saliva, blood, etc. at very high dilution levels, it may at times be necessary to make use of auxiliary magnetizable columns, filters or screens, or the addition of nickel powder to the sample, to facilitate complete separation from the sample and from unbound particles, of the low mass of superparamagnetic material actually bound to target molecules.

The following examples, which are illustrative only and in no sense limiting, illustrate how the invention works in practice:

EXAMPLE 1

A partially purified viral lysate of respiratory syncytial virus ("RSV") obtained from Chemicon (Catalog #Ag857, Lot 21031072) was diluted in an aqueous buffer of pH 7.8+0.1 having the following composition:

Tris base—24.22 grams per liter (g.p.l.)
Triton X-100—10 ml./liter
T ween 20—10 ml./liter
N-tetradecyl-N, N-dimethyl-3-ammonio-1-propane sulfonate—20.0 g.p.l.
Sodium azide—0.2 g.p.l.
Water added to make 1 liter The resulting dilution contained 0.05 mg/ml. of RSV lysate. Samples of 0.1 ml., 1 ml. and 10 ml., respectively of this dilution were carefully withdrawn after thorough mixing. To each of the 3 samples there was then added 5 microliters of approximately 250 nm average mean diameter superparamagnetic particles consisting of ferrofluid subunits of 1–30 nm diameter embedded in and each separately surrounded by BSA, which composite particles had been previously coated with anti-RSV monoclonal antibody obtained from Viro Stat, Inc. (Catalog #0631, Lot RM286). The mixture of the coated superparamagnetic particles and buffered viral lysate was in each instance thoroughly mixed and allowed to incubate for 30 minutes at room temperature on a blood bag rotator platform. Each sample was then exposed to the gradient magnetic field intensity produced by a strong rare earth permanent magnet and held stationary for at least 30 minutes, thereby concentrating the superparamagnetic conjugate and any bound RSV lysate and sequestering them in the area of greatest field intensity proximal to the magnet. In each instance the supernatant was then removed by aspiration and 100 microliters of the above-described buffer was then added.

Each of the three resulting sample concentrates was thoroughly mixed and placed in contact with a 22.5 mm wide nitrocellulose lateral flow ICT membrane (purchased from Millipore Corp. and identified as HF07504, Lot RK 000231) upon which had earlier been immovably striped across its width in the "capture" zone (located in the area most remote from the point of sample introduction) the same anti-RSV-monoclonal antibody referred to above. The contact with the nitrocellulose membrane, in each instance was initiated through an absorbent bridging pad, whereby the magnetic complex with analyte bound thereto was caused to migrate laterally through the strip to the capture line, along which magnetic conjugate bound to the viral lysate analyte bound, but magnetic conjugate free of viral lysate did not bind and was allowed to flow into an absorbent zone positioned after the capture line. In each instance the magnetic signal in millivolts of the capture line was read with the Quantum Design instrument referred to above. The exact procedure was repeated for each sample using run buffer alone, without the present of RSV viral lysate, as a negative control. The measured results are shown in the following Table 1:

TABLE #1

| RSV Lysate Concentration in mg 1 ml | Measured Signal in mV | | |
| --- | --- | --- | --- |
| | 0.1 ml sample | 1.0 ml sample | 10 ml. sample |
| 0 | 7.3 | 17.6 | 12.60 |
| 0.05 | 41.2 | 218.2 | 408.20 |

The results set forth in Table 1 are graphed in FIG. 1 hereof, wherein the intensity of magnetically induced signal is represented as a straight line function of RSV lysate concentration in mg./ml. for each sample volume assayed.

The signal to noise ratio and the detection limit in mg./ml. for each sample were calculated and the results appear in the following Table 2:

TABLE #2

RSV Lysate Concentration 0.05 mg. per ml.

| | Signal to Noise Ratio | Detection Limit in mg./ml. |
| --- | --- | --- |
| 0.1 ml. sample | 5.6 | 0.027 |
| 1.0 ml. sample | 12.5 | 0.012 |
| 10 ml. sample | 32.4 | 0.0046 |

Later work has shown that the total sensitivity of antigenic detection for each sample volume can be increased if multiple fixed stripes of antibody are applied to the ICT membrane, each spaced apart from one another along the sample flow path and the total magnetic moment of these capture lines is measured.

This example as presented illustrates the efficacy and feasibility of the superparamagnetic particles of this invention, when coated with an appropriate biological ligand such as the antibody employed in the work underlying this example, and thus enabling extraction of a biological ligand from a dilute solution in which it occurs and thereby also concentrating the ligand. It also illustrates the efficacy and practicality involved in using the same superparamagnetic particles as tags for the biological ligand in an ensuing ICT assay.

EXAMPLE 2

This example involves a possible use of the superparamagnetic particles described herein in an experimental ICT test for quantifying *Legionella pneumophila* serogroup 1 in environmental water. The present commercially available test is described in copending, commonly assigned U.S. application Ser. No. 09/458,998 filed Dec. 10, 1999 as a continuation-in-part of copending, commonly assigned U.S. application Ser. No. 09/139,770 filed Aug. 25, 1998.

In this experiment, two 100 ml. samples of cooling tower water were drawn at Hood Dairy, Portland, Me. and held at temperature of 2–8° C. To one of these samples was added sufficient *Legionella pneumophila* serogroup 1 bacteria to enrich the sample bacteria content by 95 colony-forming units ("CFU") per ml. Both samples were subjected to a filtration concentration on a small pore membrane as described in detail in copending U.S. application Ser. No. 09/458,998. The particulate retained on the membrane was recovered on a swab in each instance and was reconstituted to a sample volume of 200 μl with a buffer composition composed of aqueous 0.05 M Tris HCl and 2.5% Tween 20 having a pH of 7.0±0.1. Each sample was then carefully split into two portions. All four resulting samples were of equal volume.

Particles of approximately 100 nm average mean diameter composed of ferrofluid subunits, each of 1–30 nm average mean diameter, distributed in an enveloping matrix of BSA were coated with anti-*Legionella pneumophila* serogroup 1 antibodies which had been purified as described in copending U.S. application Ser. No. 09/139,720. Equal amounts of the resulting conjugate were added to all four of the samples and allowed to incubate for 15 minutes. One sample having no added *Legionella pneumophila* serogroup 1 bacteria and one samples having 95 CFu/ml of added bacteria were immediately subjected to an ICT test performed with a dipstick style lateral flow device comprising a nitrocellulose membrane pretreated by the application of a fixed stripe of purified anti-*Legionella pneumophila* serogroup 1 antibodies at the end of the strip most remote from the point of sample-introduction. The test strips and sample in each instance were not washed; once the samples had migrated to the end of the nitrocellulose membrane, the conductivities in millivolts (mV) of the capture lines were read by the Quantum Design instrument referred to above. The sample having no added bacteria gave a negative reading of −248.4 mV, which is believed attributable to the presence in the sample of particulate that was not broken down. The sample with added bacteria (95 CFU/ml) gave a reading of 375 mV.

The remaining two samples were each washed 3 times with 500 ml. of the buffer and then reconstituted to 100 μl and run in the same manner in identical ICT test, to first two samples. The magnetic moments of the capture lines of each of the respective test strips were read in the Quantum Design instrument. The washed sample having no added bacteria gave a reading of 8.5 mV. The washed sample with added bacteria gave a reading of 161.8 mV.

The example supports the broad concept of superparamagnetic ally separating the target ligand—in this instance the O-polysaccharide antigen of *Legionella pneumophila* serogroup 1—from a liquid sample, using superparamagnetic particles, followed by conducting an immunoassay using the same supermagnetic label for detection.

Those skilled in the art will recognize many opportunities for making use of the particles and methods referred to herein beyond the possibilities explicitly disclosed. It is therefore intended that the scope of this invention be limited only by the appended claims.

We claim:

1. A process for (1) separating a target biological ligand known to be, or suspected of being, present in dilute concentration in an aqueous fluid and (2) determining the amount of said target ligand so separated, which process comprising the steps of
   (a) coating with a first biological binding partner for said target biological ligand a group of superparamagnetic particles, which particles have an average mean diameter of at least about 100 nm and are each composed of discrete subunits of superparamagnetic material, which subunits have an average mean diameter of 1–30 nm and are separately spaced apart from one another within a covering matrix of non-metallic, non-magnetic material that is compatible with, but non-reactive with, said biological ligand and its first biological binding partner,
   (b) immersing the coated superparamagnetic particles from step (a) in a sample of said aqueous fluid which is known to contain, or is suspected of containing, said target biological ligand and allowing said particles and said fluid to incubate for a time sufficient to enable the target biological ligand, if present, to react with its first biological binding partner coated on said particles, thereby forming complexes,
   (c) exposing said complexes to a gradient of a magnetic field whereby the complexes acquire a magnetic charge and are attracted toward one another and away from the bulk of said fluid,
   (d) removing said fluid from said complexes by any suitable means,
   (e) washing said complexes and adding them to a small volume of an aqueous buffer to form a dispersion of said complexes in said buffer,
   (f) applying said dispersion to the sample receiving end of an immunochromatographic ("ICT") device configured as a dipstick and comprising a strip of bibulous material having at least one immovable stripe of a second binding partner for said target biological ligand which has been previously permanently affixed thereto at the end thereof remote from said sample receiving end,
   (g) allowing said dispersion to migrate along said strip of bibulous material and contact said at least one immovable stripe of a second binding partner for said biological ligand, whereby said target biological ligand on the surface of said complexes binds to its second binding partner on said at least one immovable stripe,
   h) measuring the magnetic charge intensity of said at least one immovable stripe, and
   i) determining from a previously established standard curve, obtained by constructing a plot of measurements of magnetic charge intensity against amount of biological ligand present, obtained when a series of standardized samples each containing a different known amount of the target biological ligand were tested in the foregoing process, the amount of biological ligand present in the fluid sample.

2. A process according to claim 1 in which said aqueous fluid is of environmental origin.

3. A process according to claim 1 in which said aqueous fluid is of mammalian origin.

4. A process according to claim 3 in which said aqueous fluid is urine.

5. A process according to claim 1 in which said first biological binding partner and said second biological binding partner have the same composition.

6. A process according to claim 1 in which said first biological binding partner and said second biological binding partner are of different composition from one another.

7. A process according to claim 1 in which the discrete subunits having an average diameter of 1–30 nm of the superparamagnetic particles subjected to coating in step (a) are discrete particles of ferrofluid and the covering matrix of nonmetallic, nonmagnetic material by which they are separately spaced apart from one another is bovine serum albumen.

8. A process according to claim 1 in which the ICT device of step (f) comprises a strip of bibulous material having multiple immovable stripes, arranged in parallel spaced apart relationship from one another, of said second binding partner for the target biological ligand are permanently affixed thereto at the end of said strip remote from its sample receiving end;
   in step (g) said dispersion migrates along said strip of bibulous material and is allowed to contact each of said multiple immovable stripes of said second binding partner for said target biological ligand, whereby some portion of said target biological ligand on the surface of said complexes in the sample reacts with said second binding partner immobilized on each of said stripes and the complexes are thereby concentrated along each said stripe;
   in step (h) the magnetic charge intensity of each immobilized stripe is measured and the measured magnetic intensities of each of the immovable stripes are added to obtain a total value; and
   in step (j) the total measured magnetic charge intensity of all the stripes is correlated, using said previously established standard curve, to the total amount of target biological ligand in the fluid sample.

9. A process according to claim 8 in which the aqueous fluid is of environmental origin.

10. A process according to claim 8 in which the aqueous fluid is of mammalian origin.

11. A process according to claim 10 in which the aqueous fluid is urine.

12. A process according to claim 8 in which said first biological binding partner and said second biological binding partner have the same composition.

13. A process according to claim 8 in which said first biological binding partner and said second biological binding partner are of different composition from one another.

14. A process according to claim 8 in which the discrete subunits having an average diameter of 1–30 nm of the superparamagnetic particles subjected to coating in step (a) are discrete particles of ferrofluid and the covering matrix of nonmetallic, nonmagnetic material by which they are separately spaced apart from one another is bovine serum albumen.

* * * * *